(12) United States Patent
West

(10) Patent No.: US 12,104,809 B2
(45) Date of Patent: Oct. 1, 2024

(54) ROBUST GAS SENSOR FOR HARSH ENVIRONMENTS

(71) Applicant: Therm-O-Disc Incorporated, Mansfield, OH (US)

(72) Inventor: Jeffrey A. West, Bellville, OH (US)

(73) Assignee: Therm-O-Disc, Incorporated, Mansfield, OH (US)

( * ) Notice: Subject to any disclaimer, the term of this patent is extended or adjusted under 35 U.S.C. 154(b) by 292 days.

(21) Appl. No.: 17/717,573

(22) Filed: Apr. 11, 2022

(65) Prior Publication Data

US 2022/0341612 A1    Oct. 27, 2022

Related U.S. Application Data

(60) Provisional application No. 63/179,790, filed on Apr. 26, 2021.

(51) Int. Cl.
  *F24F 11/36*    (2018.01)
  *F24F 11/89*    (2018.01)
  *G01D 11/24*    (2006.01)

(52) U.S. Cl.
  CPC .............. *F24F 11/36* (2018.01); *F24F 11/89* (2018.01); *G01D 11/245* (2013.01); *F25B 2500/222* (2013.01)

(58) Field of Classification Search
  CPC ........ F25B 2500/222; F25B 49/00–046; F24F 11/36; F24F 11/39; F24F 11/89; G01D 11/24; G01D 11/245
  See application file for complete search history.

(56) References Cited

U.S. PATENT DOCUMENTS

| 6,644,047 | B2 | 11/2003 | Taira et al. |
| 7,814,757 | B2 | 10/2010 | Zima et al. |
| 10,041,818 | B2 | 8/2018 | Graff et al. |

(Continued)

FOREIGN PATENT DOCUMENTS

| CN | 104089383 A | 10/2014 |
| CN | 106016450 A | 10/2016 |

(Continued)

OTHER PUBLICATIONS

Written Opinion of the IPEA for PCT/US2022/025989, ISA/EPO, mailed Mar. 23, 2023.

(Continued)

*Primary Examiner* — Justin N Olamit
(74) *Attorney, Agent, or Firm* — Harness, Dickey & Pierce, P.L.C.

(57) ABSTRACT

A sensor assembly including a housing having an inlet an outlet and an interior space generally closed from an environment external to the sensor assembly. The interior space of the housing can include an inlet zone, a central zone and an outlet zone. A baffle can be disposed within the central zone of the interior space of the housing and be located between the inlet zone and the outlet zone and nearer to the inlet zone than to the outlet zone. The baffle can extend downwardly from an upper side of the housing. A gas sensor that can be operable to detect a presence of a lower GWP refrigerant can be disposed in the outlet zone of the interior space of the housing. The housing includes a door in a lower side of the housing in the central zone of the housing.

7 Claims, 4 Drawing Sheets

(56) References Cited

U.S. PATENT DOCUMENTS

| | | |
|---|---|---|
| 10,488,065 B2 | 11/2019 | Chen et al. |
| 10,634,404 B2 * | 4/2020 | Obara .................... F25B 49/02 |
| 11,662,110 B2 * | 5/2023 | Notaro .................... F24F 11/77 |
| | | 165/11.1 |
| 2012/0079871 A1 | 4/2012 | Williamson |
| 2012/0145010 A1 * | 6/2012 | Yamamoto ............. F24F 8/108 |
| | | 96/397 |
| 2016/0091241 A1 | 3/2016 | Suzuki et al. |
| 2016/0178229 A1 | 6/2016 | Chen et al. |
| 2017/0314805 A1 | 11/2017 | Ikawa et al. |
| 2018/0313591 A1 | 11/2018 | Obara et al. |

FOREIGN PATENT DOCUMENTS

| | | |
|---|---|---|
| EP | 3159633 B1 | 8/2019 |
| EP | 3607250 A1 | 2/2020 |
| JP | 2019052785 A | 4/2019 |
| WO | 2015029094 A1 | 3/2015 |
| WO | 2016046960 A1 | 3/2016 |
| WO | 2016103785 A1 | 6/2016 |
| WO | 2017002213 A1 | 1/2017 |
| WO | 2017002215 A1 | 1/2017 |
| WO | 2018198165 A1 | 11/2018 |
| WO | 2019016959 A1 | 1/2019 |
| WO | 2019030796 A1 | 2/2019 |
| WO | 2019097607 A1 | 5/2019 |
| WO | 2019138533 A1 | 7/2019 |
| WO | 2019162993 A1 | 8/2019 |
| WO | 2019234902 A1 | 12/2019 |
| WO | 2019245669 A1 | 12/2019 |
| WO | 2020055685 A1 | 3/2020 |

OTHER PUBLICATIONS

International Search Report and Written Opinion of the ISA for PCT/US2022/025989, ISA/EPO, mailed Jul. 28, 2022.

* cited by examiner

ROBUST GAS SENSOR FOR HARSH ENVIRONMENTS

CROSS-REFERENCE TO RELATED APPLICATIONS

This application claims the benefit of U.S. Provisional Application No. 63/179,790, filed on Apr. 26, 2021. The entire disclosure of the above application is incorporated herein by reference.

TECHNICAL FIELD

The invention set forth in the appended claims relates generally to air conditioning systems and more particularly, but without limitation, to leak detection systems and sensors for use in air conditioning systems.

BACKGROUND

Hydrocarbon-based refrigerants have been used as working fluids in the heat pump and refrigeration cycle of conventional air conditioning systems. Fluorocarbons, such as chlorofluorocarbons (CFC), hydrochlorofluorocarbons (HCFC) and hydrofluorocarbons (HFC) became commonplace in air conditioning and refrigeration systems in the 20th century due to their favorable thermodynamic properties, their non-flammability, and their non-toxicity. However, while the inert nature of many CFCs and HCFCs made them preferred choices for use as refrigerants in air conditioning systems for many years, that same inert nature contributed to their long lifecycles in the atmosphere. After the discovery of ozone holes in the stratosphere over the polar regions in the early 1980s, air conditioning systems transitioned to hydrofluorocarbon (HFC) refrigerants which were not ozone depleting, such as R-134a, R-143a, and R-410A. In the early 21st century, new refrigerants were developed to be even safer for the environment. These new refrigerants are commonly referred to as lower global warming potential (GWP) refrigerants.

The American Society of Heating, Refrigeration, and Air Conditioning Engineers (ASHRAE) has promulgated standards classifying various refrigerants according to their toxicity and flammability. For example, ASHRAE Standard 34 classifies refrigerants having a lower toxicity as Class A refrigerants, and refrigerants having a higher toxicity as Class B refrigerants. The flammability class of refrigerants is determined according to ASTM E681, Standard Test Method for Concentration Limits of Flammability of Chemicals (Vapors and Gases) at a temperature of 60° C. and a pressure of 101 kPa. According to ASHRAE Standard 34, Class 1 refrigerants do not propagate a flame, Class 2L refrigerants have a lower flammability and a slow flame propagation (for example, a burning velocity less than 10 cm/s), Class 2 refrigerants have lower flammability and faster flame propagation (for example, a burning velocity of greater than 10 cm/s), while Class 3 refrigerants have a higher flammability and faster flame propagation (for example, a burning velocity greater than 10 cm/s). Under the ASHRAE Standard 34, the commonly used R-410A refrigerant has a Class A toxicity classification and a Class 1 flammability classification. Thus, R-410A is referred to as an A1 refrigerant under ASHRAE Standard 34.

New lower GWP refrigerants include but are not limited to refrigerants such as R-1234yf, R-1234ze, R-32, R-454A, R-454C, R-455A, R-447A, R-452B, and R-454B. These refrigerants have a Class A toxicity classification and a Class 2L flammability classification under ASHRAE Standard 34. Thus, these refrigerants may be referred to as A2L refrigerants. Because A2L refrigerants have the ability to propagate a flame, precautions must be taken to prevent the accidental build-up of A2L refrigerants, particularly in enclosed spaces. However, A2L refrigerants will not ignite if their concentration level is below their lower flammability limit. Thus, there is the need to provide apparatus, systems, and methods for detecting A2L refrigerant leaks and the build-up of A2L refrigerants in air conditioning systems.

SUMMARY

New and useful systems, apparatuses, and methods for providing a refrigerant sensor are set forth in the appended claims. Illustrative embodiments are also provided to enable a person skilled in the art to make and use the claimed subject matter.

For example, in some embodiments, a sensor assembly may include a housing having an inlet and an outlet. A diverter wall may be disposed within the housing between the inlet and outlet. A refrigerant sensor may be disposed without the outlet.

In other aspects of the disclosure, a sensor assembly can have a housing comprising and inlet, an outlet and an interior space generally closed from an environment external to the sensor assembly. The interior space of the housing can include an inlet zone, a central zone and an outlet zone. A baffle can be disposed within the central zone of the interior space of the housing and be located between the inlet zone and the outlet zone and nearer to the inlet zone than to the outlet zone. The baffle can extend downwardly from an upper side of the housing. A gas sensor can be disposed in the outlet zone of the interior space of the housing. In such a construction, the housing is configured to enable gas from the environment to pass through the interior space of the housing, with the gas entering at the inlet and moving from the inlet zone to the central zone to the outlet zone and exiting at the outlet. The baffle is configured to interrupt a laminar flow of the gas and create a turbulent flow of the gas in the central zone of the interior space of the housing.

In still other aspects of the disclosure, the sensor assembly includes a gas sensor that can be operable to detect a presence of a lower GWP refrigerant. Further, the gas sensor can be operable to detect a presence of an A2L refrigerant.

In yet other aspects of the disclosure, the sensor assembly can provide that the housing includes a door in a lower side of the housing in the central zone of the housing. The door can be positionable in an opened condition and a closed condition.

Alternatively, the door can be being permanently fixed in an opened condition. The door can have a wall that is slanted from a first end affixed to the lower side of the housing to a second end at an opening of the door.

Still further, a refrigeration system comprising the sensor assembly is provided.

In still other aspects of the disclosure, a refrigerant sensor unit can alternatively include a housing defining a cavity within the housing, an inlet fluidly coupled to the cavity and an outlet fluidly coupled to the cavity. The cavity can include an upper side and a lower side. The outlet can be disposed nearer to the upper side of the cavity than to the lower side of the cavity. A diverter wall can be disposed within the cavity and project from the upper side of the cavity, The diverter wall can extend from the upper side of the cavity toward the lower side of the cavity. A sensor operable to detect a presence of an A2L refrigerant can be disposed within the cavity and near the outlet of the housing.

Alternatively, still other example embodiments may include a refrigerant sensor unit having a housing member defining a cavity within the housing member. An inlet may be fluidly coupled to the cavity. An outlet may also be fluidly coupled to the cavity. A refrigerant sensor may be disposed within the outlet. A diverter wall may be disposed within the cavity and coupled to the housing member at a top of the housing member. The outlet may be positioned near a top of the housing member. The diverter wall may extend from the top of the housing member towards a bottom of the housing member. The inlet may be in fluid communication with the outlet.

Objectives, advantages, and a preferred mode of making and using the claimed subject matter may be understood best by reference to the accompanying drawings in conjunction with the following detailed description of illustrative embodiments.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings, as applicable.

DESCRIPTION

The following description of example embodiments provides information that enables a person skilled in the art to make and use the subject matter set forth in the appended claims, but it may omit certain details already well-known in the art. The following detailed description is, therefore, to be taken as illustrative and not limiting.

Figure 1:
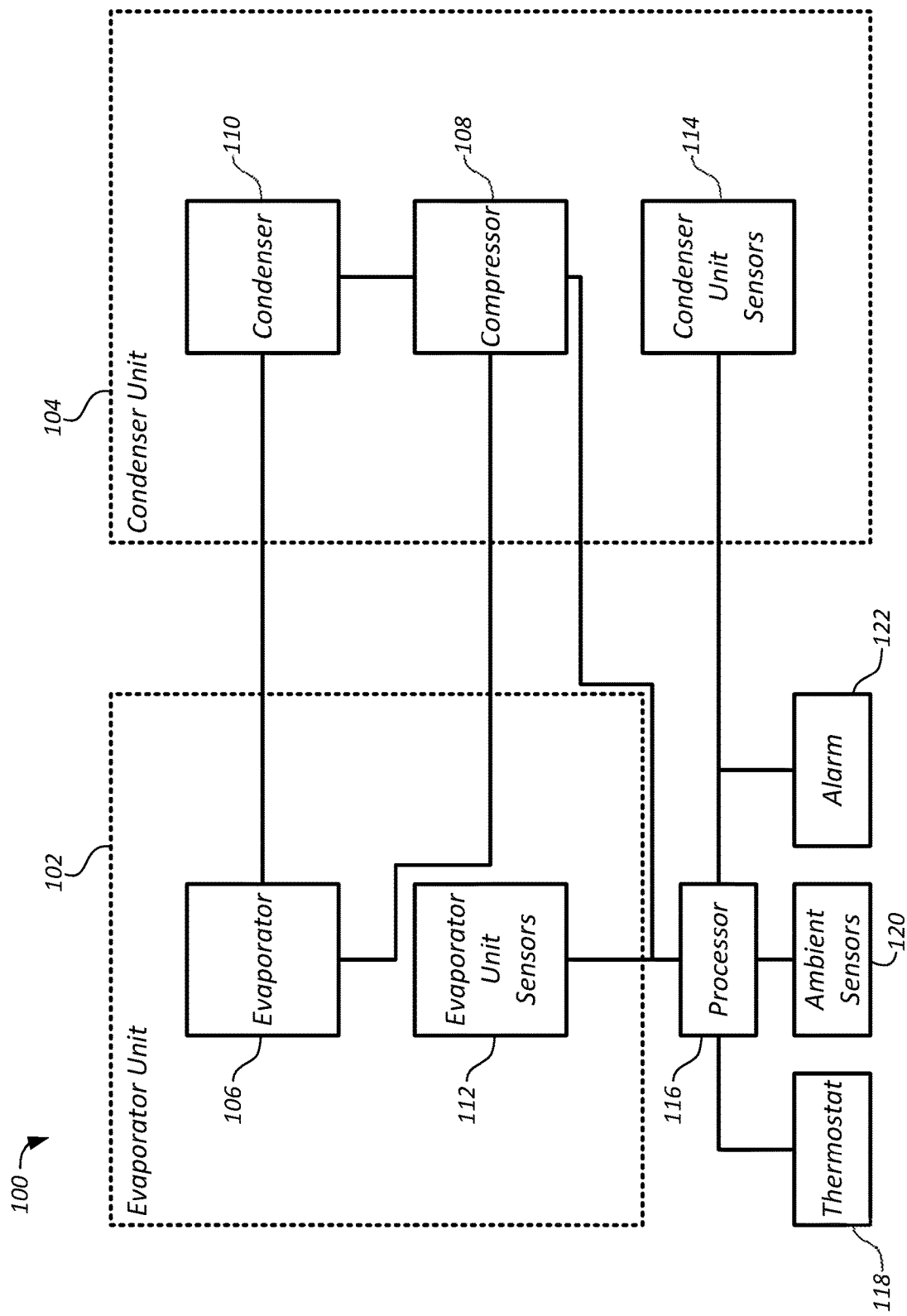
FIG. 1 is a functional block diagram of an example embodiment of a refrigeration cycle system used in heating, ventilation, and air conditioning systems.

FIG. 1 is a functional block diagram of an example embodiment of a refrigeration cycle system 100 used in heating, ventilation, and air conditioning (HVAC) systems. As shown in FIG. 1, some examples of the system 100 may include an evaporator unit 102 and a condenser unit 104. According to some examples, the evaporator unit 102 may be located indoors and referred to as an indoor unit, while the condenser unit 104 may be located outdoors and referred to as an outdoor unit. The evaporator unit 102 may include an evaporator 106, such as an evaporator coil, and the condenser unit 104 may include a compressor 108 and a condenser 110. The evaporator 106, compressor 108, and the condenser 110 may be fluidly coupled, such as by a pipe, gas line, or liquid line. For example, the evaporator 106 may be fluidly coupled to the compressor 108 by a suction line. In some examples, the evaporator 106 may be fluidly coupled to the condenser 110 by a liquid line. According to exemplary embodiments, the compressor 108 may be fluidly coupled to the condenser 110 by a hot gas line.

In operation, the compressor 108 may compress a refrigerant, such as an A2L refrigerant. For example, the A2L refrigerant may include R-1234yf, R-1234ze, R-32, R-454A, R-454C, R-455A, R-447A, R-452B, or R-454B. After the refrigerant is compressed by the compressor 108, the hot compressed refrigerant gas may be provided to the condenser 110 through the hot gas line. The condenser 110 cools the hot refrigerant gas, which condenses back into liquid refrigerant. The liquid refrigerant may be transported from the condenser 110 to the evaporator 106 through the liquid line. At the evaporator 106, the liquid refrigerant may expand back into a refrigerant gas. As a result of the refrigerant's phase change from liquid into gas in the evaporator 106, the temperature of the refrigerant is decreased, and the cooled refrigerant gas may absorb heat energy from the evaporator 106, cooling the exterior of the evaporator 106 in the process. A fan (not shown) may provide airflow over the cooled exterior of the evaporator 106. As the air flows over the cooled exterior of the evaporator 106, the evaporator 106 may absorb heat energy from the flowing air, cooling the air. This cooled air may then be provided via ductwork to an air conditioned environment, such as the interior of a room within a building.

The system 100 may also include various monitoring and control means, such as sensors, thermostats, and processors. For example, evaporator unit sensors 112 may be provided within a housing member of the evaporator unit 102, and condenser unit sensors 114 may be provided within a housing member of the condenser unit 104. The evaporator unit sensors 112 and condenser unit sensors 114 may be operatively coupled to a processor 116. In some examples, a thermostat 118 may be provided to monitor the refrigerated environment. The thermostat 118 may also be operatively coupled to the processor 116. In illustrative embodiments, additional ambient sensors 120 may also be provided and operatively coupled to the processor 116. The evaporator unit sensors 112, condenser unit sensors 114, and/or ambient sensors 120 may include sensors suitable for detecting a presence of a refrigerant, such as a lower GWP refrigerant and/or an A2L refrigerant. Upon detecting the presence of the refrigerant, the evaporator unit sensors 112, condenser unit sensors 114, and/or the ambient sensors 120 may send a signal to the processor 116. Based on the signal from the evaporator unit sensors 112, condenser unit sensors 114, and/or the ambient sensors 120, the processor 116 may cause the system 100 to cease operation, such as by sending a signal to the compressor 108 to stop. In some examples, based on the signal from the evaporator unit sensors 112, condenser unit sensors 114, and/or the ambient sensors 120, the processor 116 may send a signal to an alert or notification device, such as an alarm 122, to produce an audible, visual, or haptic warning to a user.

Figure 2:
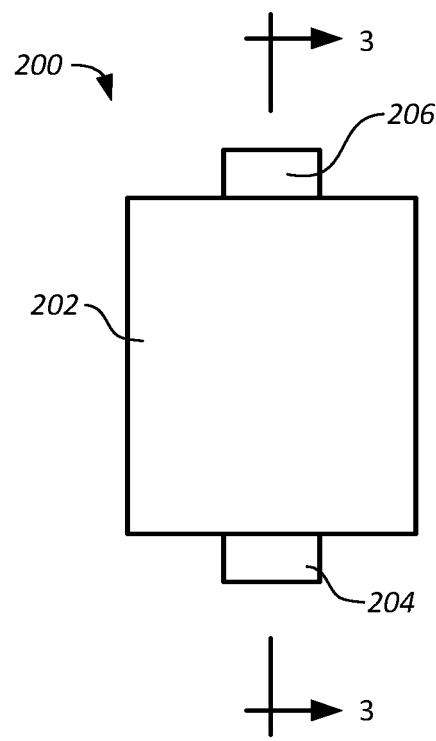
FIG. 2 is a top view of some examples of a sensor assembly, which may be associated with some examples of the evaporator unit sensors, condenser unit sensors, and/or ambient sensors of the system of FIG. 1.

FIG. 2 is a top view of some examples of a sensor assembly 200, which may be associated with some examples of the evaporator unit sensors 112, condenser unit sensors 114, and/or ambient sensors 120 of the system 100 of FIG. 1. For example, the evaporator unit sensors 112, condenser unit sensors 114, and/or the ambient sensors 120 may each include one or more of the sensor assembly 200. Each sensor assembly 200 may include an external housing, such as a housing 202. The housing 202 may further include a first opening such as inlet 204 at a first end of the housing 202, and a second opening such as outlet 206 at a second end of the housing 202. In some examples, the first end and the second end may be at opposite sides of the housing 202.

Figure 3:
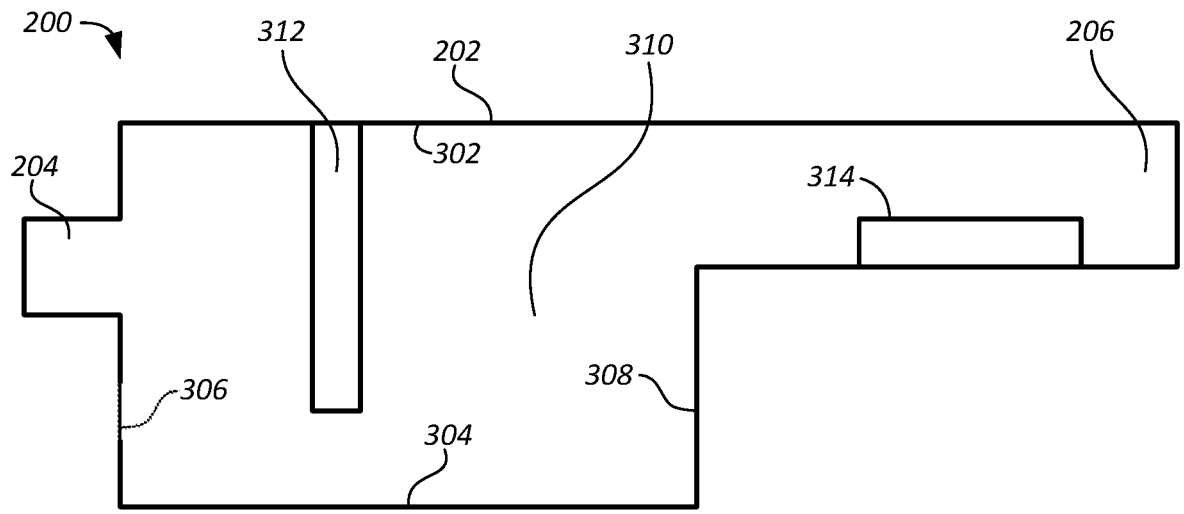
FIG. 3 is a cross-sectional view of the sensor assembly of FIG. 2, taken at line 3-3, and illustrating additional details that may be associated with some embodiments of the sensor assembly.

FIG. 3 is a cross-sectional view of the sensor assembly 200 of FIG. 2, taken at line 3-3, and illustrating additional details that may be associated with some embodiments of the sensor assembly 200. For example, as shown in FIG. 3, the housing 202 may include a first wall portion 302, a second wall portion 304, a third wall portion 306, and a fourth wall portion 308. Wall portions 302, 304, 306, and 308 may define an interior space of the sensor assembly 200, such as cavity 310. A baffle or diverter wall 312 may be disposed within the cavity 310. A refrigerant sensor, such as sensor 314, may be disposed within the housing 202. The housing 202 may be any shape suitable to contain the diverter wall 312 and/or the refrigerant sensor 314. For example, the housing 202 may define a substantially cuboidal shape or a substantially cylindrical shape. In examples where the housing 202 is a cuboid, the wall portions 302, 304, 306, and 308 may be substantially planar members, such as substantially rectangular planar members. In some examples, the housing 202 may be substantially cylindrical. Accordingly, the wall portions 302 and 304 may be opposite portions of a continuous surface, such as a curved side, while the wall portions 306 and 308 may be substantially circular. While the wall portions 302, 304, 306, and 308 are described as substantially planar members or surfaces, each of the wall portions 302, 304, 306, and 308 may have a thickness.

In some examples, as shown in FIG. 3, the diverter wall 312 may be coupled to or project from the first wall portion 302, preferably near the inlet 204 and/or nearer to the inlet 204 than to the outlet 206. According to illustrative embodiments, the diverter wall 312 extends a distance from the first wall portion 302 toward the second wall portion 304 such that an end of the diverter wall 312 may be close to the second wall portion 304, but does not touch the second wall portion 304. As shown in FIG. 3, in some examples, the sensor 314 may be disposed in the outlet 206. In some examples, the sensor 314 may be disposed within the cavity 310, for example, on the first surface 302, or on a surface of the diverter wall 312 opposite the inlet 204, or on the fourth wall 308. As illustrated in FIG. 3, in some examples, the outlet 206 may be located near the top region of the sensor assembly 200. For example, the outlet 206 may be located proximate the first wall portion 302.

Figure 4:
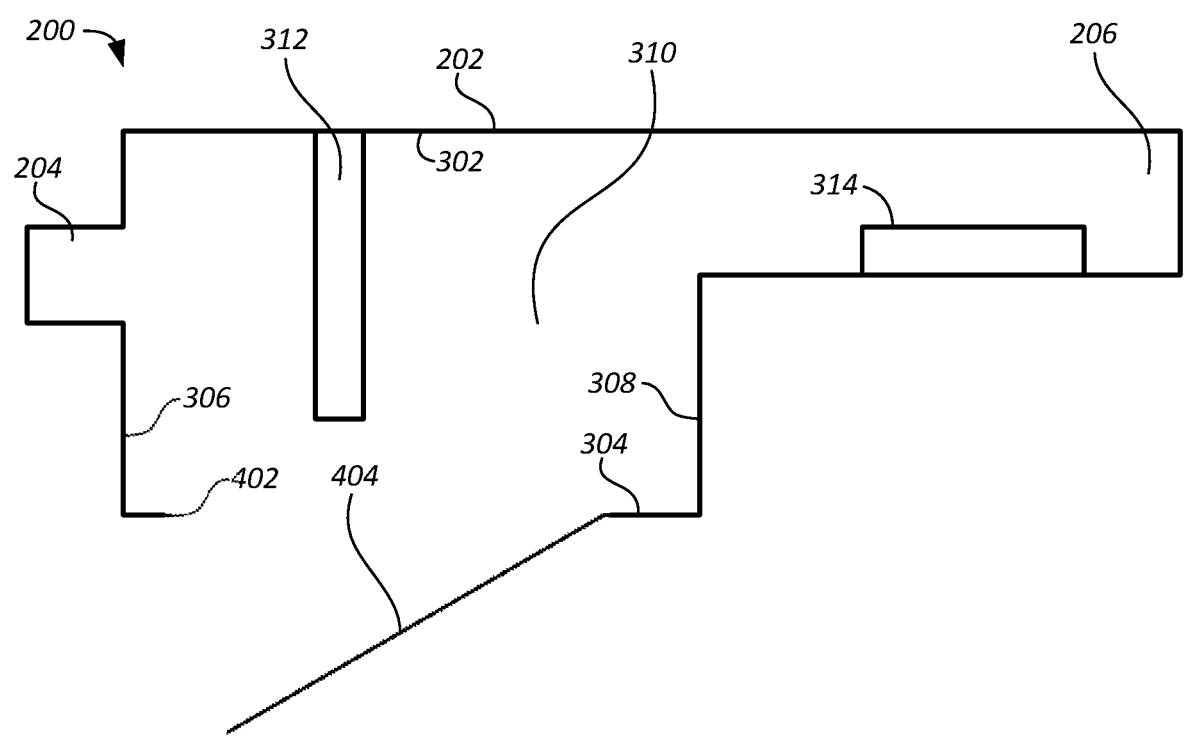
FIG. 4 is a cross-sectional view illustrating additional details that may be associated with some examples of the sensor assembly.

FIG. 4 is a cross-sectional view illustrating additional details that may be associated with some examples of the sensor assembly 200. For example, the second wall portion 304 may further include an opening 402. A cover, such as a removable cover or a door 404 may be positioned over the opening 402 in order to provide a substantial seal between the cavity 310 and the external environment. In some examples, the door 404 may be opened and closed as desired by the user.

Figure 5:
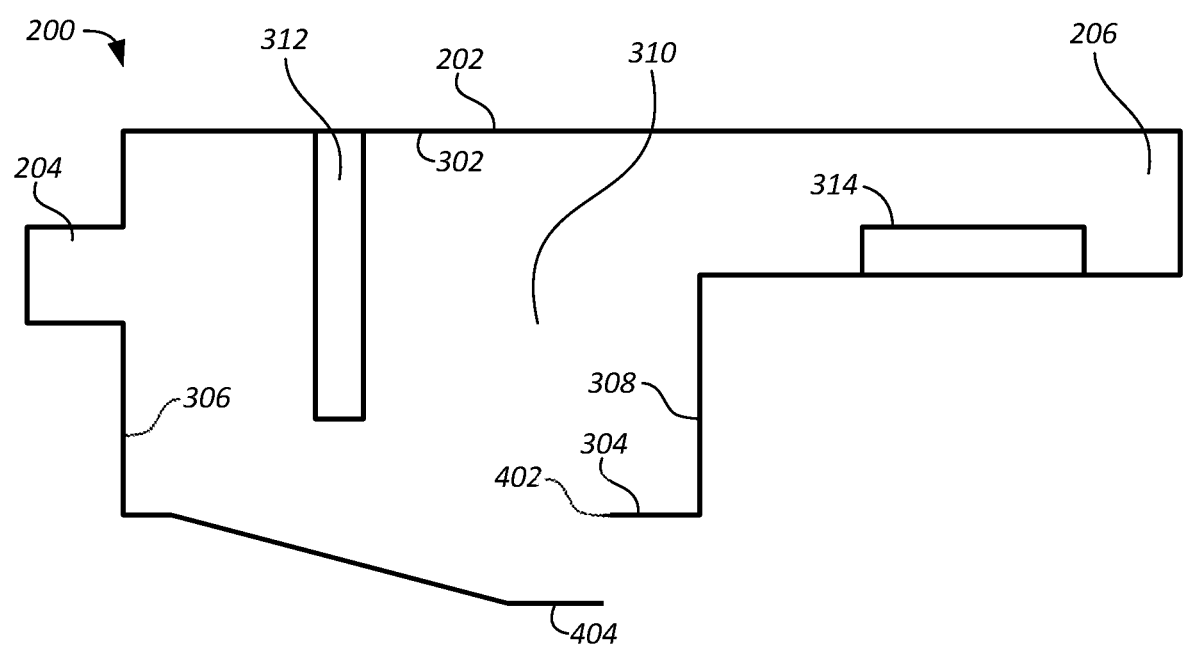
FIG. 5 is a cross-sectional view illustrating additional details that may be associated with some examples of the sensor assembly.

FIG. 5 is a cross-sectional view illustrating additional details that may be associated with some examples of the sensor assembly 200. In various implementations, the door 404 may also be a fixed structure. For example, the door 404 may be integrally formed with the housing 202, and remain fixed in an open position to allow the cavity 310 to remain open to the external environment through the opening 402. The door 404 can include a wall that is slanted from a first end that is affixed to the lower side of the housing and extend to a second end at an opening of the door 404.

The systems, apparatuses, and methods described herein may provide significant advantages. For example, sensing A2L refrigerant leaks in residential and commercial HVAC applications or refrigeration applications may be challenging due to the presence of lint, dirt, oils, and other foreign materials or debris within the HVAC system or refrigeration system. With conventional sensor housings, these foreign materials may potentially clog the sensor inlet, preventing leaked refrigerant gas from reaching the sensor. The sensor assembly 200 provides a physical dirt and oil trap that has the advantage of not requiring a filter.

In operation, gas may enter the sensor assembly 200 from the inlet 204. After entering the cavity 310 from an external environment through the inlet 204, the flow of the gas may be disrupted by the diverter wall 312. For example, if the gas flow was substantially laminar upon entering the inlet, the diverter wall 312 may disrupt the laminar gas flow and create a substantially turbulent region between the inlet 204 and the diverter wall 312. Any foreign materials carried by the laminar gas stream would enter the turbulent region and be pulled by gravity towards the second wall 304 at the bottom of the housing 202. In some examples, the diverter wall 312 may direct the gas flow towards the bottom of the housing 202, causing the foreign materials to be carried towards the second wall 304 along with the gas flow. Thus, foreign materials which may have entered the sensor assembly 200 may become trapped near the bottom of the housing 202. For example, foreign materials may be trapped by gravity near the second wall 304.

As previously described, in some examples, the outlet 206 may be located near the top of the sensor assembly 200, such as near the first wall 302 and away from the bottom of the sensor 200 and second wall 304. Accordingly, in examples where the sensor 314 is disposed in the outlet 206, the sensor 314 is located away from contact with any foreign materials trapped near the bottom of the cavity 310. Similarly, in examples where the sensor 314 is coupled to the first wall 302, or to a surface of the diverter wall 312 opposite the inlet 204, or to the fourth wall 308 near the outlet 206, the sensor 314 may be positioned away from contact with any trapped foreign materials. In some examples, such as where the sensor assembly 200 includes the opening 402 and the door 404, the door 404 may be opened in order to remove foreign materials which may have collected within the cavity 310. Thus, the sensor assembly 200 may be easily serviced by the user, reducing the overall operating costs associated with the system 100.

In various implementations, the door 404 may be integrally formed with the body 202 of the sensor assembly 200, reducing manufacturing costs by eliminating the need to produce a separate door, hinge mechanism, and latch.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A gas sensor assembly, comprising:
    a housing configured to enable a flow of gas from an environment external to the housing to move through the housing;
    wherein the housing defines an interior space at least partially separated from the environment external to the housing and comprises an inlet, an outlet, an upper wall, a lower wall, a diverter wall, and a wall portion located between the upper wall and the lower wall;
    wherein the housing further defines an inlet zone comprising the inlet, a central zone located downstream of the inlet zone and comprising the diverter wall and a portion of the interior space of the housing between a side of the diverter wall opposite to the inlet and the wall portion, and an outlet zone located downstream of the central zone and comprising the outlet;
    wherein the housing is configured to enable the flow of gas to enter at the inlet, move from the inlet zone to the central zone to the outlet zone and exit at the outlet;
    wherein the diverter wall is located nearer the inlet zone than the outlet zone;
    wherein the diverter wall is connected to the upper wall of the housing and projects from the upper wall of the housing into the interior space of the housing and ends near the lower wall of the housing;
    wherein the outlet is located at an upper side of the gas sensor assembly and away from the lower wall;
    wherein a gas sensor is disposed in the outlet zone of the housing and is configured to be exposed to the flow of gas exiting the housing;
    wherein the diverter wall is configured to create a turbulent flow of the gas in the central zone and to direct any foreign material carried by the gas toward the lower wall of the housing and away from the gas sensor before the gas flows into the outlet zone; and
    wherein the gas sensor is operable to detect a presence of an A2L refrigerant.

2. The gas sensor assembly of claim 1 wherein the gas sensor is operable to detect a presence of at least one of R-1234yf, R-1234ze, R-32, R-454A, R-454C, R-455A, R-447A, R-452B and R-454B refrigerants.

3. The gas sensor assembly of claim 1 wherein the housing further comprises a door included in the lower wall of the housing in the central zone of the housing, the door being positionable in an opened condition and a closed condition.

4. A refrigeration system comprising the gas sensor assembly of claim 3.

5. The gas sensor assembly of claim 1 wherein the housing further comprises a door included in the lower wall of the housing in the central zone of the housing, the door being permanently fixed in an opened condition.

6. The gas sensor assembly of claim 5 wherein the door comprises an inclined wall that is slanted from a first end affixed to the lower wall of the housing to a second end at an opening of the door.

7. A refrigeration system comprising the gas sensor assembly of claim 6.

* * * * *